(12) United States Patent
Juan

(10) Patent No.: US 6,783,364 B1
(45) Date of Patent: Aug. 31, 2004

(54) FAST CONNECTOR OF A WATER-SPRAY TOOTH CLEANER

(76) Inventor: Chung-Chun Juan, No. 179, Sec. 1, Chang Mei Road, Chang Hua City (TW)

( * ) Notice: Subject to any disclaimer, the term of this patent is extended or adjusted under 35 U.S.C. 154(b) by 164 days.

(21) Appl. No.: 10/244,843

(22) Filed: Sep. 17, 2002

(51) Int. Cl.[7] .............................................. A61B 17/02
(52) U.S. Cl. ........................................ 433/80; 601/165
(58) Field of Search ............................ 433/80; 601/162, 601/163, 164, 165

(56) References Cited

U.S. PATENT DOCUMENTS 6,006,374 A * 12/1999 Winnett et al. ................. 4/525

* cited by examiner

Primary Examiner—Cary E. O'Connor
Assistant Examiner—Candice C. Melson
(74) Attorney, Agent, or Firm—Charles E. Baxley

(57) ABSTRACT

A water-spray tooth cleaner includes a faucet connector and a water inlet tube. The faucet connector is provided with a water canal, an assembly slot, and a locating piece slidably disposed in the assembly slot such that a through slot of the locating piece is aligned with the water canal. The through slot is provided in the inner wall with a retaining projection. The water inlet tube is provided at a connection end with an engagement end which is provided in the outer wall with a retaining groove. The connection end of the water inlet tube is detachably connected to the water canal of the faucet connector such that the retaining groove of the engagement end is detachably engaged with the retaining projection of the through slot of the locating piece.

2 Claims, 7 Drawing Sheets

FAST CONNECTOR OF A WATER-SPRAY TOOTH CLEANER

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates generally to a water-spray tooth cleaner, and more particularly to a connector of the water-spray tooth cleaner for connecting the tooth cleaner to a faucet spout.

BACKGROUND OF THE INVENTION

The conventional water-spray tooth cleaner is generally provided with a connector by which the conventional water-spray tooth cleaner is connected to a faucet spout. The connector is provided with a plurality of bolts for locating the connector such that the inner ends of the bolts press against the outer wall of the faucet spout. The connector is rather primitive in design because it cannot be fastened to and unfastened from the faucet spout with ease and speed, and because the connector is susceptible to separation from the faucet spout by the water pressure. The use of the bolts to locate the connector often results in water leaks. In addition, the chore of tightening and loosening the bolts is not only time-consuming but also irritating, thereby discouraging people to use the water-spray tooth cleaner.

BRIEF SUMMARY OF THE INVENTION

The primary objective of the present invention is to provide a water-spray tooth cleaner with a fast connector to facilitate the connecting of the water-spray tooth cleaner to a faucet spout.

The fast connector is provided in the interior with a water canal extending along the longitudinal direction of the connector. The connector is further provided with an assembly slot perpendicular to the water canal and extending through the water canal. The assembly slot is used to accommodate a locating piece which is provided with a through slot and a knob. The through slot is provided in the inner wall with a retaining projection. The connector is fastened at the top end with the faucet spout such that the water canal and the through slot of the locating piece are aligned with the faucet spout.

The water-spray tooth cleaner is provided with an inlet tube which is in turn provided with a connection end. In operation, the connection end of the inlet tube is retained by the retaining projection of the through slot of the locating piece. The connection end of the inlet tube can be easily disconnected with the locating piece by pushing the locating piece to cause the retaining projection of the through slot of the locating piece to separate from the connection end.

The features, functions, and advantages of the present invention will be more readily understood upon a thoughtful deliberation of the following detailed description of a preferred embodiment of the present invention with reference to the accompanying drawings.

DETAILED DESCRIPTION OF THE INVENTION

Figure 1:
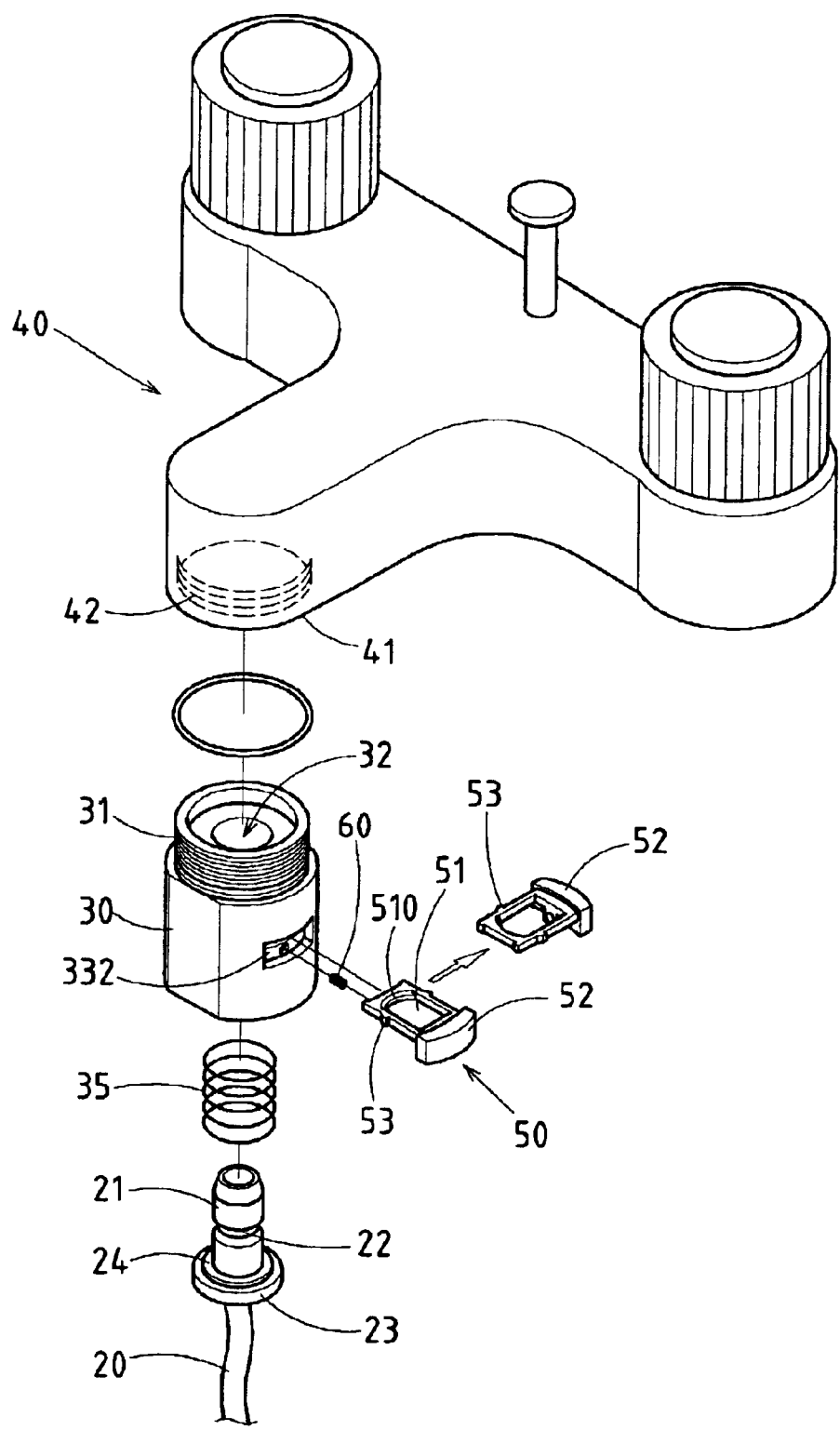
FIG. 1 shows an exploded perspective view of the preferred embodiment of the present invention.
Figure 2:
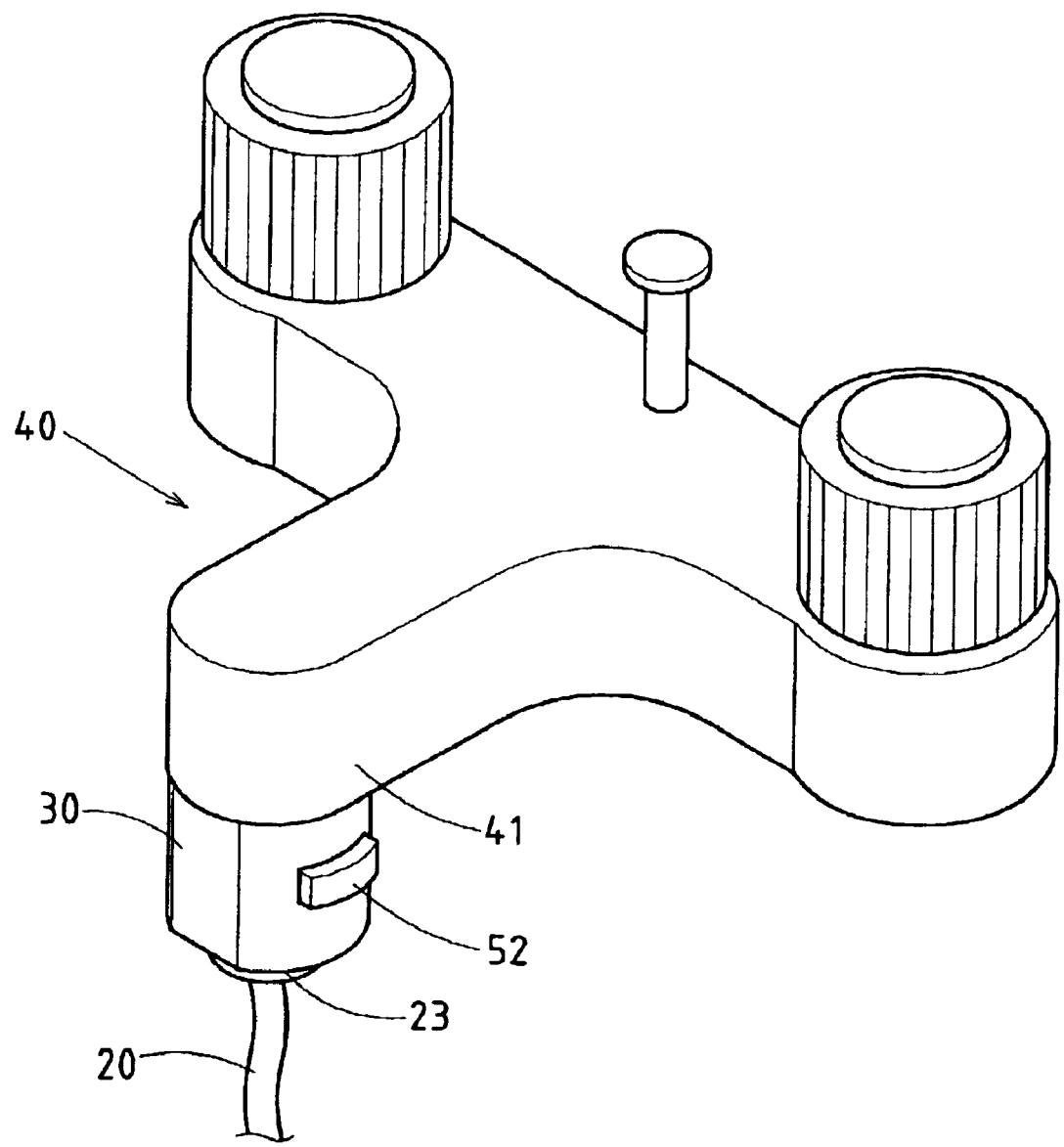
FIG. 2 shows a perspective view of the preferred embodiment of the present invention with a water faucet spout.

As shown in FIGS. 1–7, a water-spray tooth cleaner 10 embodied in the present invention comprises an inlet tube 20 and a faucet connector 30.

The inlet tube 20 is provided at a connection end thereof with a connection disk 23, a protrusion 24 extending from the connection disk 23, and an engagement end 21. The engagement end 21 is provided in the outer wall with a groove 22.

Figure 3:
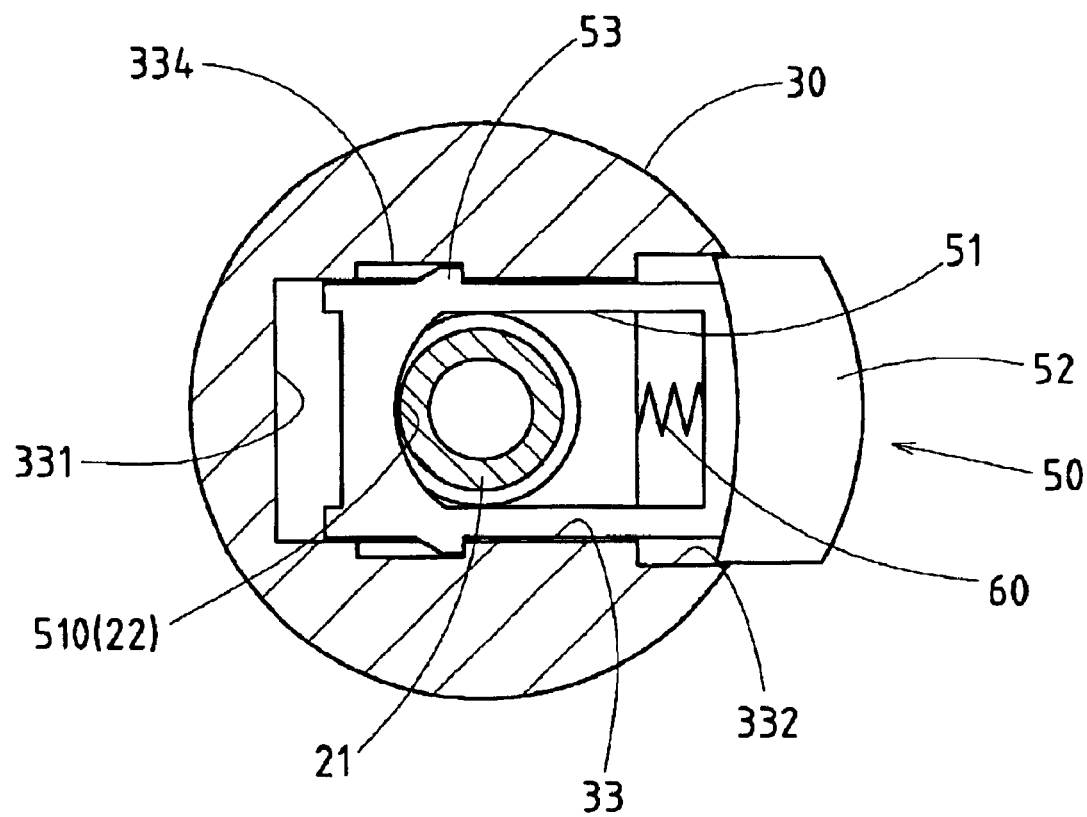
FIG. 3 shows a cross-sectional view of the preferred embodiment of the present invention.

The faucet connector 30 is provided in the outer wall of a top end thereof with outer threads 31 engageable with inner threads 42 of the spout 41 of a water faucet 40, as shown in FIG. 1. The connector 30 is provided in the interior with a water canal 32 and an assembly slot 33. The water canal 32 is extended through both longitudinal ends of the connector 30, while the assembly slot 33 is perpendicular to the water canal 32 such that the assembly slot 33 is extended through the water canal 32. The connector 30 is further provided with a locating piece 50, which is slidably received in the assembly slot 33. The locating piece 50 is provided with a through slot 51 and a knob 52. The locating piece 50 is received in the assembly slot 33 in such a manner that the through slot 51 is aligned with the water canal 32, and that the knob 52 is jutted out of the connector 30. The assembly slot 33 is provided at the open end with a receiving slot 332 corresponding in size and shape to the knob 52 of the locating piece 50. Located between the bottom wall of the receiving slot 332 and the inner wall of the knob 52 is a recovery spring 60. The assembly slot 33 is provided in proximity of a closed end 331 with two arresting cavities 334, whereas the locating piece 50 is provided in proximity of the inner end thereof with two retaining protuberances 53 corresponding in location to the arresting cavities 334. The locating piece 50 is securely retained in the assembly slot 33 such that the retaining protuberances 53 are securely retained in the arresting cavities 334, as shown in FIG. 3.

Figure 4:
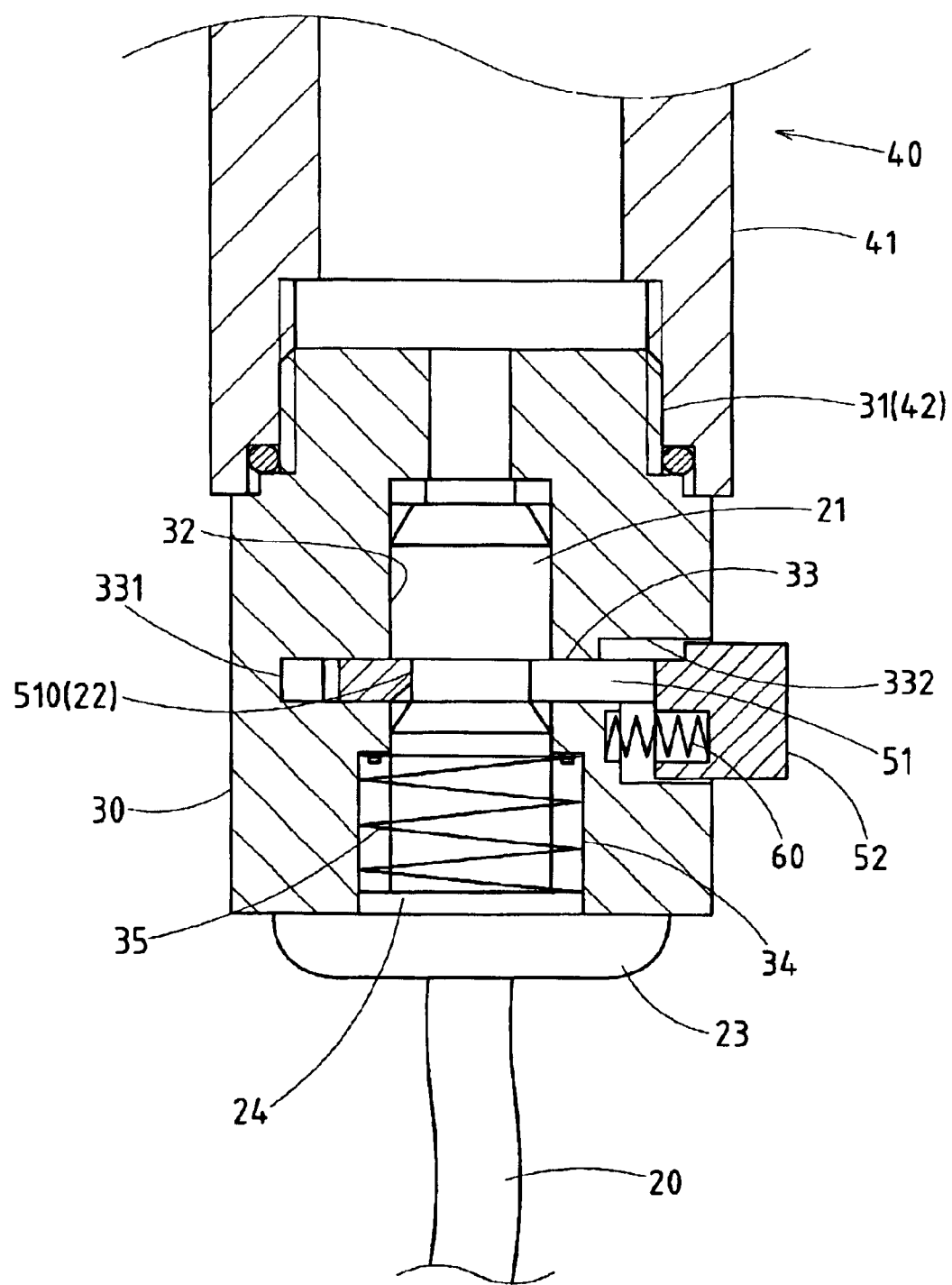
FIG. 4 shows a longitudinal sectional view of the preferred embodiment of the present invention.
Figure 5:
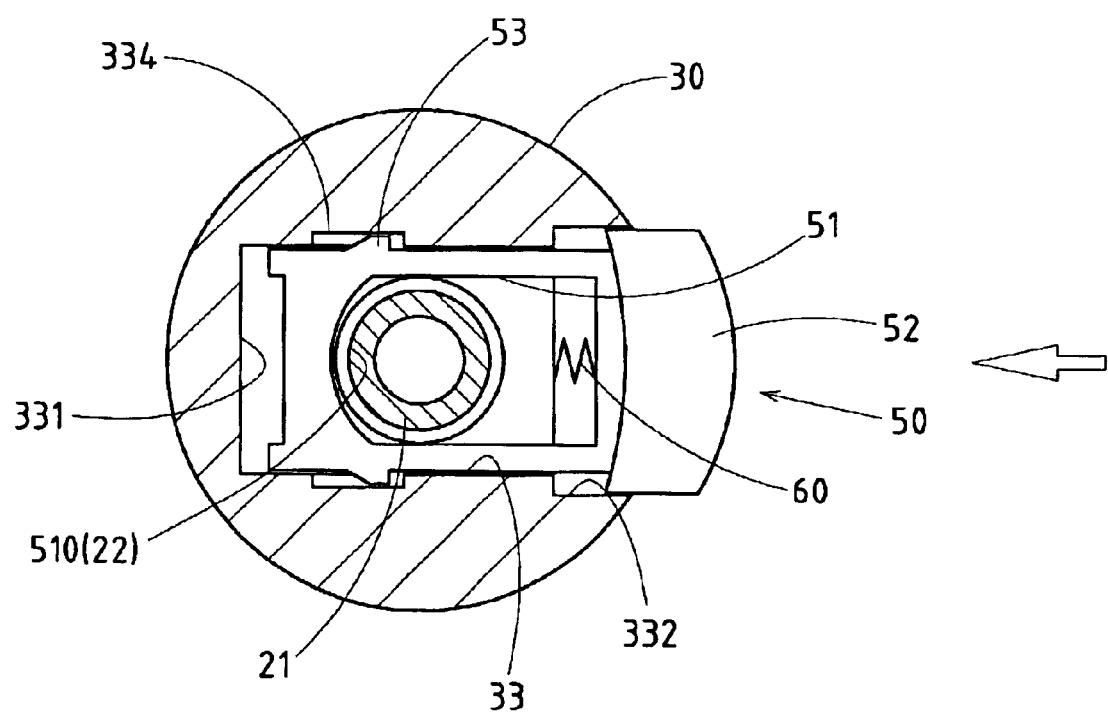
FIG. 5 is across-sectional view to show the separating of the connection end of the inlet tube from the locating piece of the preferred embodiment of the present invention.

As shown in FIG. 4, the water canal 32 of the faucet connector 30 is provided in the bottom end with a receiving portion 34 and a spring 35 which is received in the receiving portion 34 such that the spring 35 is compressed in the receiving portion 34 by the protrusion 24 of the connection end of the water inlet tube 20 at the time when the connection end of the water inlet tube 20 is detachably fastened with the faucet connector 30 in such a manner that the engagement end 21 is inserted into the water canal 32, and that the groove 22 of the engagement end 21 is engaged with a retaining projection 510 of the inner wall of the through slot 51 of the locating piece 50, and that the connection disk 23 of the connection end of the water inlet tube 20 comes in a close contact with the wall of the bottom end of the water canal 32.

Figure 6:
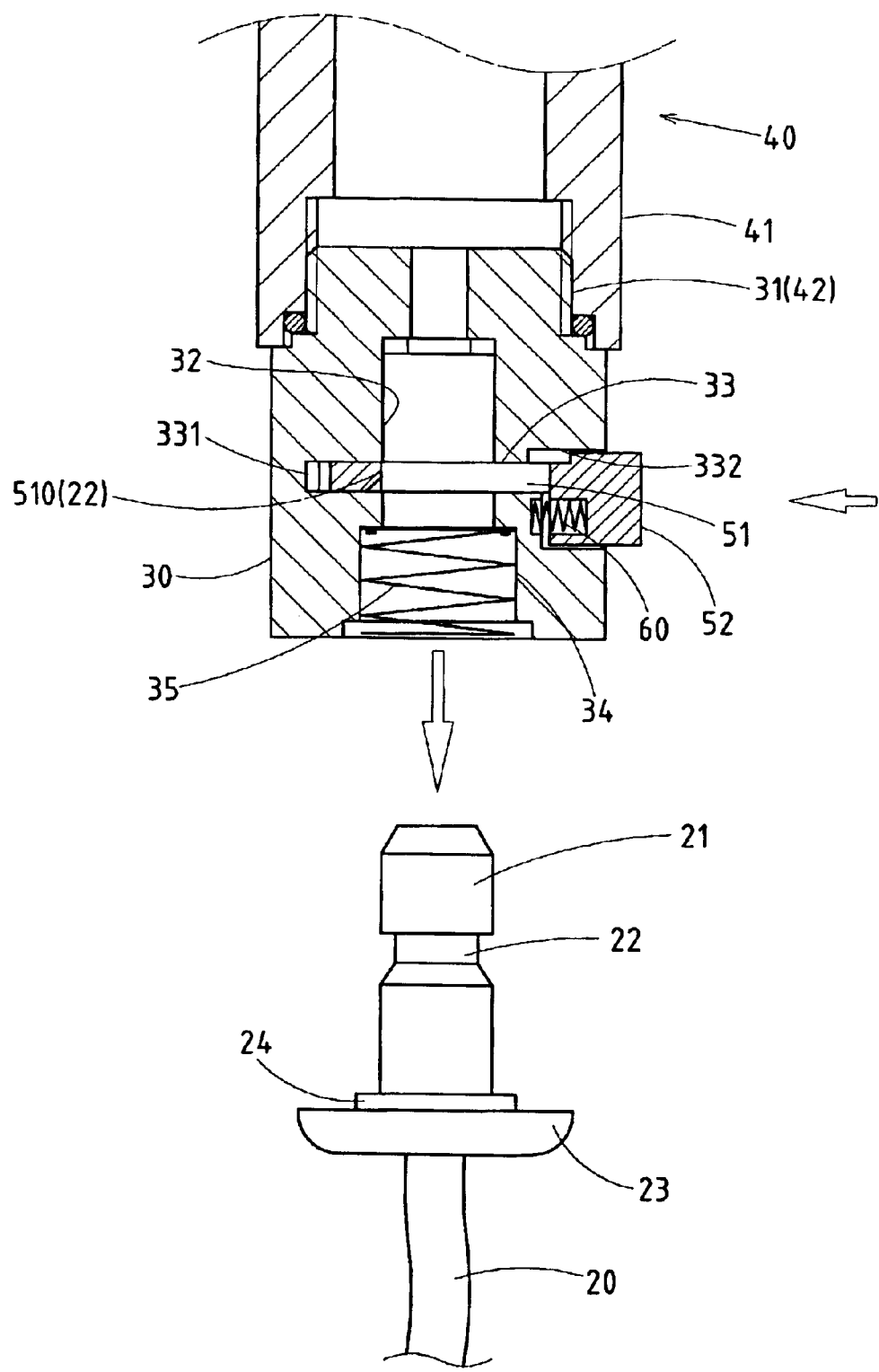
FIG. 6 shows a longitudinal sectional view of the preferred embodiment of the present invention as shown in FIG. 5.
Figure 7:
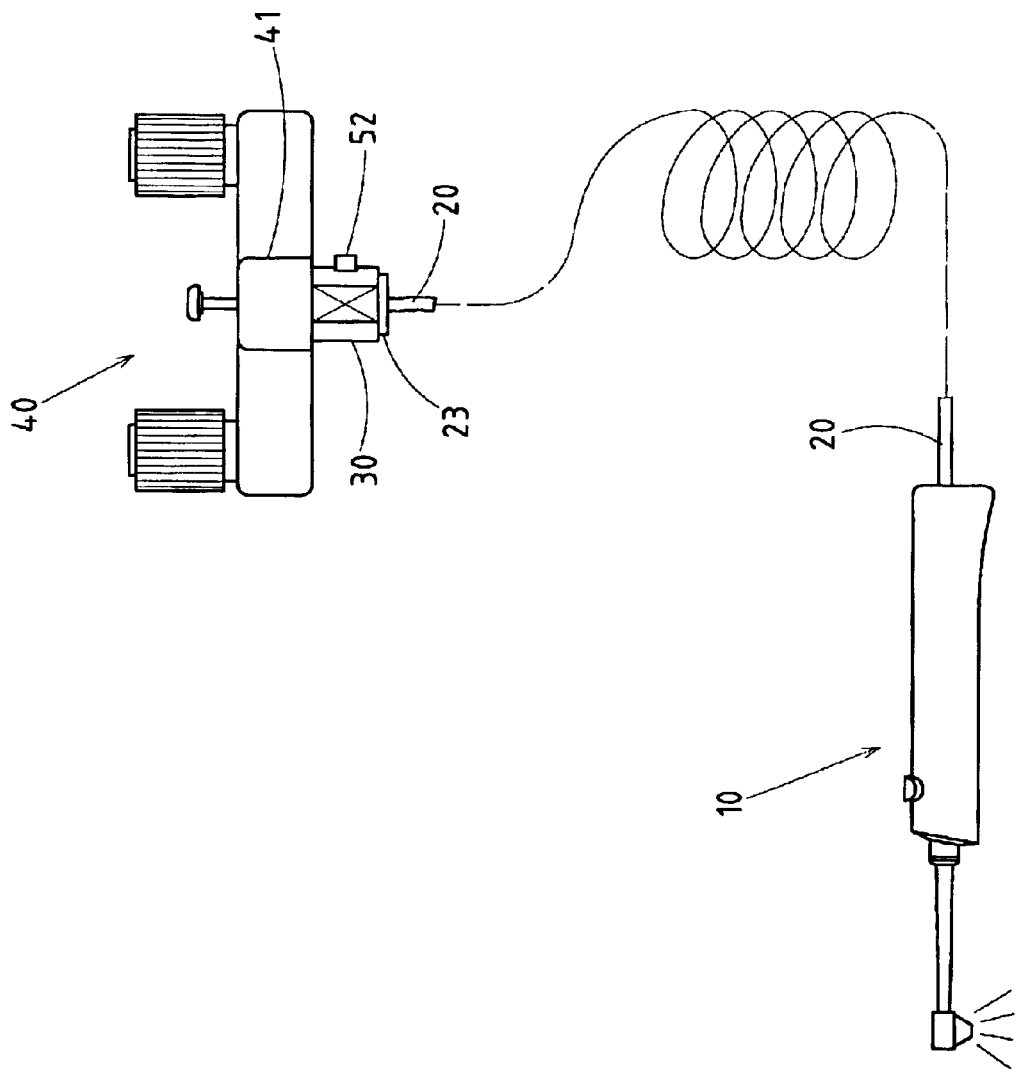
FIG. 7 shows a schematic plan view of the preferred embodiment of the present invention in operation.

As shown in FIG. 6, the connection end of the of the inlet tube 20 is ejected by the spring force of the spring 35 on the heels of an event in which the knob 52 of the locating piece 50 is pushed by an external force, thereby resulting in separation of the retaining projection 510 from the groove 22 of the engagement end 21. The faucet connector 30 may be permanently fastened with the water faucet spout 41, without obstructing the function of the water faucet spout 41.

The embodiment of the present invention described above is to be regarded in all respects as being illustrative and nonrestrictive. Accordingly, the present invention may be embodied in other specific forms without deviating from the spirit thereof. The present invention is therefore to be limited only by the scope of the following claims.

I claim:

1. A water-spray tooth cleaner comprising:

a faucet connector provided in an interior with a water canal extending through a longitudinal top end and a longitudinal bottom end of said faucet connector, said faucet connector being fastened at the longitudinal top end thereof to a faucet spout such that said water canal is in communication with the faucet spout; and a water inlet tube detachably connected at a connection end thereof to said water canal of said, faucet connector;

wherein said faucet connector is comprised of, in the interior, an assembly slot and a locating piece slidably disposed in said assembly slot, said assembly slot being perpendicular to said water canal and extending through said water canal, said assembly slot comprising an open end and a closed end which is comprised of two arresting cavities, the open end being comprised of a receiving slot, said locating piece comprised of a through slot, two retaining protuberances corresponding in location to said arresting cavities of said closed end of said assembly slot, and a knob corresponding in shape and size to said receiving slot of the open end of said assembly slot whereby said locating piece is disposed in said assembly slot in conjunction with a recovery spring such that said through slot is aligned with said water canal of said faucet connector, and that said two retaining protuberances of said locating piece are slidably retained in said two arresting cavities of the closed end of said assembly slot, and that said recovery spring is located between said receiving slot of the open end of said assembly slot and an inner wall of said knob of said locating piece, with said knob being partially received in said receiving slot of the open end of said assembly slot whereby said through slot of said locating piece is provided in an inner wall with a retaining projection; and wherein said water inlet tube is comprised of, at the connection end thereof, a connection disk and an engagement end extending from said connection disk, said engagement end being provided in an outer wall with a groove whereby said water inlet tube is detachably connected to said faucet connector in such a manner that said engagement end is inserted into said water canal of said faucet connector, and that said groove of said engagement end is detachably engaged with said retaining projection of said through slot of said locating piece, and that said connection disk comes in contact with the longitudinal bottom end of said faucet connector.

2. The water-spray tooth cleaner as defined in claim 1, wherein said water canal of said faucet connector is comprised of, in a bottom end, a receiving portion and a spring compressibly received in said receiving portion; wherein said water inlet tube is further provided at the connection end thereof with a protrusion extending from said connection disk such that said protrusion is located between said connection disk and said engagement end whereby said engagement end is put through said spring, with said protrusion pressing against one end of said spring so as to cause said spring to compress in said receiving portion of the bottom end of said water canal.

* * * * *